United States Patent [19]

Teitelbaum

[11] 4,199,424
[45] Apr. 22, 1980

[54] PROTECTIVE SHIELD FOR SENSING MEANS

[75] Inventor: Bernard R. Teitelbaum, Birmingham, Mich.

[73] Assignee: The Bendix Corporation, Southfield, Mich.

[21] Appl. No.: 941,883

[22] Filed: Sep. 13, 1978

[51] Int. Cl.² .......................................... G01N 27/58
[52] U.S. Cl. ..................... 204/195 S; 73/23
[58] Field of Search .............. 204/195 S, 1 S; 60/276; 123/119 E, 119 EC; 324/29; 73/23, 53, 61 R, 61.1 R

[56] References Cited

U.S. PATENT DOCUMENTS

| | | | |
|---|---|---|---|
| 3,369,346 | 2/1968 | Wildbolz et al. | 73/23 X |
| 3,835,012 | 9/1974 | Hemak | 204/195 S |
| 3,844,920 | 10/1974 | Burgett et al. | 204/195 S |
| 3,869,370 | 3/1975 | Sayles | 204/195 S |
| 3,960,693 | 6/1976 | Weyl et al. | 204/195 S |
| 4,038,034 | 7/1977 | Nakajima et al. | 23/255 E |
| 4,063,897 | 12/1977 | Aoki | 23/254 E |
| 4,065,372 | 12/1977 | Hacker et al. | 204/195 S |
| 4,098,653 | 7/1978 | Kita et al. | 204/1 T |
| 4,140,611 | 2/1979 | Yaegashi et al. | 204/195 S |

Primary Examiner—G. L. Kaplan
Attorney, Agent, or Firm—Markell Seitzman; Russel C. Wells; James R. Ignatowski

[57] ABSTRACT

A shield for introducing fluid, such as the gas within the exhaust system of an internal combustion engine, to a sensing means such as a zirconium dioxide element of an oxygen concentration sensor. The shield forms a chamber which surrounds the element and contains a particulate trap having a preferred orientation with respect to the main stream flow for intercepting and diverting a portion of fluid from the main stream into a partially closed end of the chamber. The diverted fluid enters the chamber near the tip end of the zirconia element; the closely spaced chamber permits the fluid flow to be generally parallel to the surface of the element and directed from the tip end to the base or housing end of the element. The shield further contains an opening near the base of the element to permit fluid to exit the chamber.

13 Claims, 16 Drawing Figures

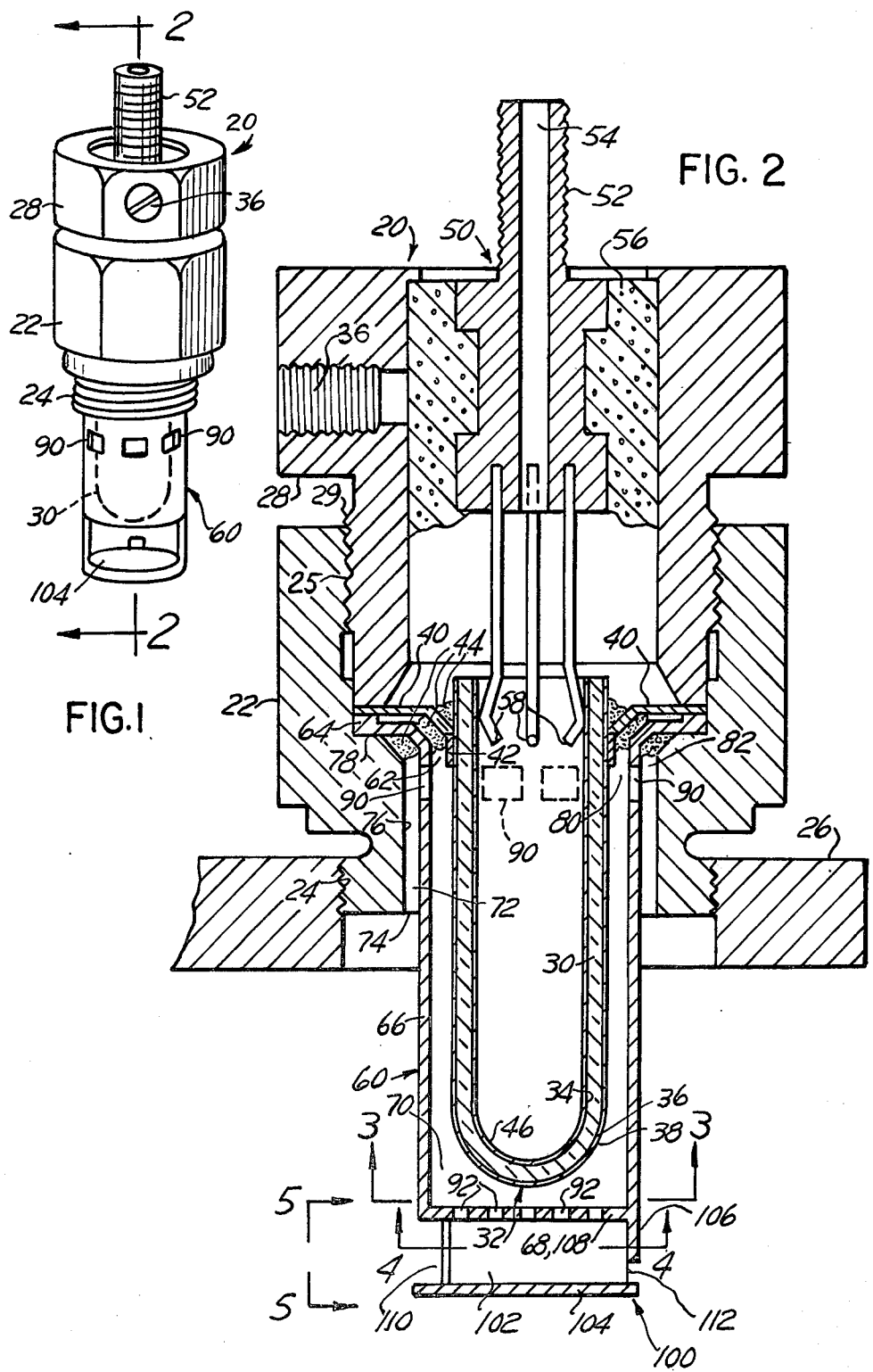

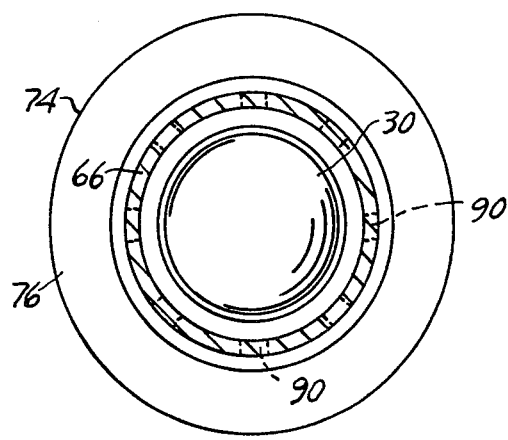
FIG.3
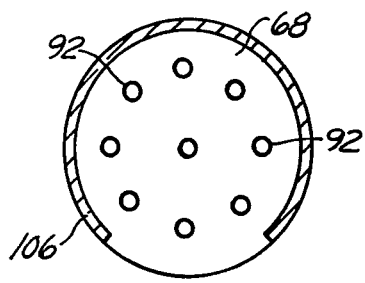
FIG.4
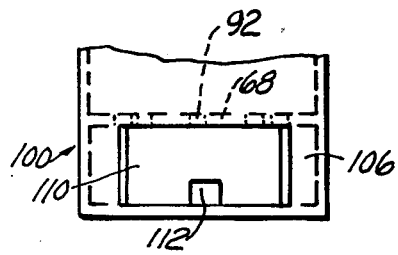
FIG.5
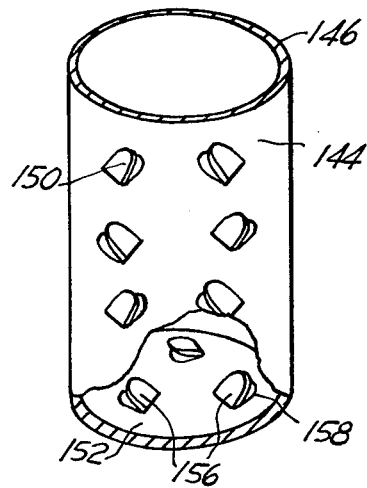
FIG.8
FIG.9

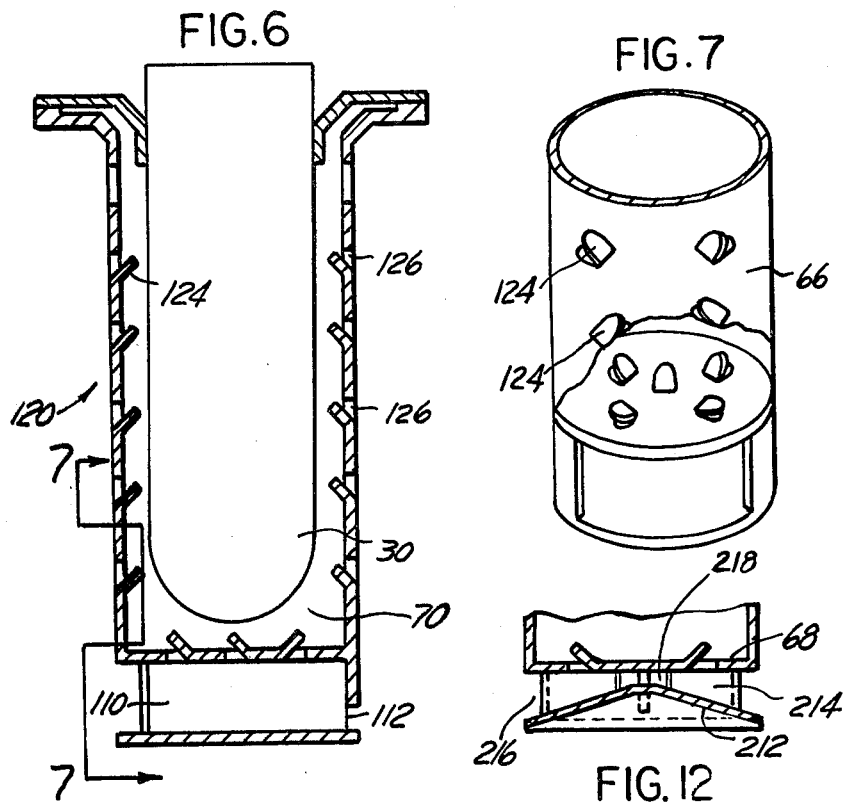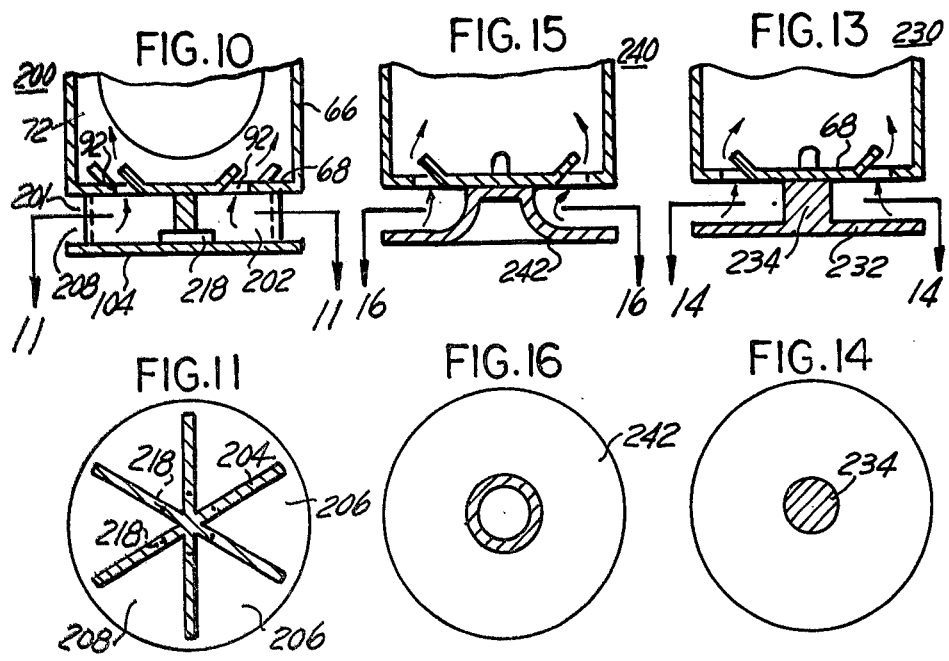

PROTECTIVE SHIELD FOR SENSING MEANS

CROSS-REFERENCE TO OTHER APPLICATIONS

The application contains subject matter similar to that in the simultaneously filed, commonly assigned, copending application Serial No. 941,882 of B. R. Teitelbaum and J. D. Bode entitled "Protective Shield Having Omnidirectional Diverter For Sensing Means," now U.S. Pat. No. 4,184,934.

BACKGROUND OF THE INVENTION

This invention is addressed to gas sensors generally and more particularly to particulate shields for oxygen sensors and to techniques for extending the useful life and for improving the efficiency of such a sensor when utilized in hostile environments, such as within the corrosive heated exhaust stream of an internal combustion engine.

It is well documented that a zirconium dioxide element when maintained at an elevated temperature can generate a voltage potential which is related to the partial pressure or concentrations of oxygen on either side of the walls of the element. More particularly, as discussed in U.S. Pat. No. 3,835,012, when a first surface of a sensor containing zirconium dioxide is exposed to a reference oxygen concentration and a second surface is exposed to an external environment having an unknown, but different, oxygen concentration, a voltage potential is generated between the first and the second surfaces. The generated voltage potential is indicative of the concentration of oxygen in the external environment surrounding the second surface of the zirconium dioxide element.

In general, the operation of this type of sensor is based upon the natural phenomena that a zirconium dioxide (zirconia) element becomes activated when heated. In particular, at elevated temperatures the zirconia element becomes conductive to oxygen ions. The oxygen ions tend to migrate through the zirconia element in the direction of the lowest concentration of oxygen wherein they become deposited on a thin layer of porous platinum lining the surfaces of the zirconia element. Platinum provides a high temperature electrical connection, as well as, acts as a catalyst to improve sensor performance.

Zirconium dioxide sensors can be inserted into the exhaust system of an internal combustion engine as disclosed by Burgett et al in U.S. Pat. No. 3,844,920. As the air/fuel ratio of the exhaust gas departs from a stoichiometric mixture, a voltage potential is generated indicative of the rich or lean oxygen content of the exhaust gas mixture.

The problems associated with the use of zirconium dioxide are numerable and are amplified when the element is used in a hostile atmosphere, such as in an automotive exhaust system. Zirconium dioxide is a fragile ceramic material and when subjected to the mechanical and thermal shock of the heated automotive exhaust system environment displays a shortened mechanical and electrical life. Mechanical strength can be enhanced by doping the zirconia element with yttrium oxides or oxides of magnesium. The effect of thermal shock can be minimized by allowing the gas to make a good thermal contact with a cooler surface, such as a protective shield, before the gas flow contacts the ceramic element. Thermodynamic design principles necessitate that there be a sufficient heat transfer capability between the gas and the protecting surface (shield) to dampen sudden changes in the gas temperature before the heated gas contacts the zirconia element thereby eliminating shock from sudden changes of the temperature of the gas. However, the protecting surface (shield) should not act as too great of a "heat sink," or the oxygen sensor will be prevented from reaching a proper operating temperature or alternatively, the time required for the sensor to reach its operating temperature will be greatly increased. Illustrative of the importance of not introducing large thermal delays into the gas measurements is that in a cold engine exhaust system environment, a thermally sluggish oxygen sensor will not be responsible to the oxygen content in the exhaust gases for an extended time after a cold start of the engine.

The reduction of the useful electrical lifetime of the oxygen sensor arises from the erosion of the external platinum coating on the zirconia element. Large scale erosion of this catalytic layer can be prevented by not allowing high velocity particulates within the gas to impinge directly upon the platinum surface. This can be effected by lowering the velocity of the gas before it flows over the zirconia element.

In addition to increasing the life of the platinum surface, it is desirable to enhance the sensitivity by using as much of the surface of the zirconia element as possible. This implies that the direction of the gas flow is preferably in a direction generally parallel to the element's central axis flowing from its tip to its base or vice versa rather than a flow pattern, which is generally perpendicular to one side of the element, as disclosed in the prior art.

Exemplary of sensors having shields which create perpendicular flow about the zirconia element in U.S. Pat. No. 3,844,820, which incorporates a plurality of vane shaped openings or U.S. Pat. No. 3,835,012 which, uses plurality of tangentially arranged perforations. A third type of protective shield having elongated flared openings is shown by Weyl et al in U.S. Pat. No. 3,960,692.

Generally, the effectiveness of the oxygen sensor is reduced by particulates which accumulate upon the zirconia element such as a carbon deposit.

It is an object of the invention to provide an improved oxygen sensor shield. It is another object of the invention to reduce the thermal shock on the ceramic zirconia element. A further object is to prevent large scale erosion of the catalytic coating on the zirconia element. Another object of this invention is to prevent the deposition of carbon and other particulates onto the sensing element.

An additional object of the invention is to improve the uniformity of heating and to increase the rate of heating of the zirconia element on an exhaust gas stream.

SUMMARY OF THE INVENTION

The invention is a solution to the aforementioned problems and consists of a shield covering a sensing element, such as the zirconium dioxide element of an exhaust gas oxygen concentration sensor. It is recognized, however, that the invention may be practiced in cooperation with other sensors in a variety of fluidic environments.

A cup-shaped shield is adapted to the housing of an oxygen concentration sensor. The shield contains a central cavity that surrounds and is spaced apart from a tubular zirconium dioxide element. The element and cavity cooperating to create a chamber therebetween wherein the gas entering the chamber is directed to flow from the tip end toward the base end of the element. The shield has a particulate trap having a receiving cavity into which a portion of the mainstream of fluid such as exhaust gas flowing in the exhaust system of an internal combustion engine, can flow. The gas within the receiving cavity will exhibit turbulence at which point carbon and other particulates will tend to accumulate in the receiving cavity and will be blown out through an exit port provided in the downstream portion of the receiving cavity.

Most of the intercepted gas will be diverted into the central chamber through a plurality of openings in the end of the shield which is adjacent to the receiving cavity. The gas entering the central chamber will have a velocity less than that of the gas in the mainstream. In addition, this gas will exhibit less rapid temperature variations than gas in the mainstream because of the heat sink qualities of the shield. Oxygen absorption may be further increased with the addition of turbulence generators on the walls of the shield surrounding the zirconia element. The gas exits from the chamber and returns to the mainstream through openings in the shield in the proximity of the base of the element. In this manner, by directing the gas to flow from tip to base, the total surface area of the sensing means is used, increasing the sensitivity of the sensor.

BRIEF DESCRIPTION OF THE DRAWINGS

In the following illustrations:

FIG. 1 is a frontal view of an oxygen sensor having a protective shield covering a zirconia element.

FIG. 2 is a view through section 2—2 of FIG. 1 showing the oxygen sensor attached into the walls of an exhaust system.

FIG. 3 is a view through section 3—3 of FIG. 2 showing the concentric mounting relationships between the oxygen sensor, the shield, and the exhaust system.

FIG. 4 is a view through section 4—4 of FIG. 2 showing the partially closed end of the shield cavity and a portion of entrance part of the particulate trap.

FIG. 5 is a frontal view of the particulate trap.

FIG. 6 is a cross-sectional view of an alternate shield having turbulence generators showing only the shield and zirconia elements.

FIG. 7 is a frontal view of the lower portion of the shield depicted in FIG. 6.

FIG. 8 is a sectional view of another embodiment of a shield having turbulence generators.

FIG. 9 is a prospective view of the basket which is part of the shield shown in FIG. 8.

FIG. 10 shows a partial side view of an omni-direction diverter.

FIG. 11 is a cross-sectional view of the trap of FIG. 10 through section 11.

FIG. 12 is a partial side view of another omni-directional diverter.

FIG. 13 is a partial side view of another omni-directional diverter.

FIG. 14 is a cross-sectional view through section 14 of FIG. 13.

FIG. 15 is a partial side view of another omni-directional diverter.

FIG. 16 is a cross-sectional view through section 16 of FIG. 15.

DETAILED DESCRIPTION

Referring to FIGS. 1 and 2 there is shown an Oxygen Sensor 20 having a Housing Element 22, an oxide ion conductive Element 30 and the disclosed Shield 60. The Housing Element 22 has a threaded portion 24 which is adapted to threadably engage mating threads disposed in a Wall 26 of an internal combustion engine exhaust system. The engagement of threaded portion 24 with the mating threads of the Wall 26 provides a rigid mounting of the Oxygen Sensor 20 to the exhaust system. The Oxygen Sensor 20 further includes a Sensor Body 28 having a threaded Portion 29 adapted to be received in a threaded Portion 25 of the Housing Element 22.

An oxygen ion conductive Element 30 having a hollow tubular shape with one enclosed End 32, is fixedly attached to the sensor Body 28. The Element 30 is preferably fabricated from a solid electrolyte such as zirconium dioxide. The Exterior Surface 36 of the zirconium dioxide Element 30 is coated with a Layer 38 of electrically conductive material that is porous to oxygen, such as a layer of platinum which also serves as a catalyst to facilitate oxygen absorption and reaction at its surface. An electrically conductive Collar 40 in combination with an electrically conductive Compression Ring 42 provides for sealing engagement of the Layer 38 to the Housing Element 22.

Additionally, the Collar 40 and Layer 38 can be positively sealed together by utilizing a Seal 44 having compatible thermal expansion characteristics to that of the oxygen ion conductive Element 30. A material compatible with the thermal characteristics of zirconium dioxide is a glass, such as Corning Glass 7056 supplied by the Corning Glass Works, Corning, N.Y. The interior Surface 34 of Element 30 is coated with a thin oxygen ion porous Layer 46 of a suitably conductive material. This coating is preferably platinum, however, it is understood that other materials performing the same function may be substituted.

An electrically conductive Member 50 having a Protusion 52 and a Bore 54 extending completely through Member 50, provides an electrical contact through Spring Wires 58 to the inside conductive Layer 46. The Bore 54 permits ambient air to be communicated to the interior of the sensor Body 28 and Element 30. The ambient air provides a reference gas having a determinable oxygen concentration. The electrically conductive Member 50 is disposed within and electrically insulated from the Sensor Body 28 by an Insulating Spacer 56, which may be a solid ceramic or formed ceramic-like cement. The insulating Spacer may be secured to the Sensor Body 28 by means of a Set Screw 36, or be spring loaded as shown in the commonly assigned application Ser. No. 857,333 filed December 5, 1977, which is expressly incorporated by reference. The plurality of spring Wires 58 attached to Member 50 extend into the interior of Element 30 and are biased to provide a multipoint electrical contact with the inner surface Coating 46.

A general description of the operation of the above-described oxygen sensor follows. Atmospheric air, having a known oxygen concentration of about 21% is communicated to the interior portion of Element 30 via the Bore 54. When the Oxygen Sensor 20 is emersed into a flow of heated exhaust gas the platinum Exterior Coating 38 of the zirconium dioxide Element 30 will be exposed to a gas having an oxygen concentration substantially below that of the reference air. Oxygen ions will migrate through the zirconium dioxide Element 30 in the direction of the lowest concentration of oxygen. These ions will deposit upon the Exterior Coating 38 producing a measurable voltage potential between the Interior 46 and Exterior Coatings 38. The Exterior Coating 38 is in electrical contact with the Walls 26 of the exhaust system component causing the Wall 26 to be at chassis ground. The migration of oxygen ions will therefore produce a positive charge on the Interior Coating 46. The magnitude of this voltage potential difference will be a function of the number of oxygen ions migrating to the Exterior Coating 38 and will therefore be a direct function of the oxygen concentration present within the exhaust system. The exhaust gases of automotive vehicles operating at an air/fuel ratio richer than the stoichiometric mixture value theoretically have a zero oxygen concentration and also have an excess of unreacted fuel. As each oxygen molecule enters the exhaust system through the Exterior Coating 38, it will be immediately reacted with an available fuel molecule due to the catalytic action of the surface coating, consequently, the oxygen concentration present at the Exterior Coating 38 will remain essentially zero for all values of air/fuel ratios less than the stoichiometric mixture value. However, at the stoichiometric mixture value and for further increasing air/fuel ratios, there should be no available fuel molecules for reaction with the arriving oxygen molecules and an oxygen concentration will accumulate in the vicinity of Exterior Coating 38. This will result in a reduced migration of oxygen molecules thereby substantially reducing the output signal which may be derived from this device.

Referring now to the lower portion of FIG. 2 and FIG. 3 there is shown further details of the Shield 60.

A cup-like Shield 60 having an Open End 62, a circumferential Flange 64 adjacent to the Open End 62, a cylindrical Wall 66 and a partially Closed End 68, encloses the exposed portion of the ion conductive Element 30. The space between the Shield 60 and the Element 30 forms a generally cylindrical Chamber 70. The Shield 60 is received within a Bore 76 of the Housing Element 22 and extends outwardly through an Aperture 74 formed in the Housing 22. The exterior dimensions of the Wall 66 and the interior dimensions of the Aperture 74 are sized to permit the Wall 66 to be spaced apart from the Aperture 74 forming an annular Cavity 72. The concentricity of the Shield 60 relative to Aperture 74 and the Element 30 is achieved by the close spacing between the Flange 64, Collar 40 and Bore 72. A circumferential Shoulder 78 at the base of Bore 72 positions the Shield 60 in the axial direction.

The Collar 40, Flange 64 and Shoulder 78 are maintained in positive engagement by the Sensor Body 28 threaded into the threaded Portion 25 of the Housing Element 22. The sandwiching of the Collar 40 and the Shoulder 64 against the Shoulder 78 closes the upper Ends 80, 82 of the Chamber 70 and the Cavity 72 respectively. Additional sealing may be affected by introducing a Glass Seal 44 at the Ends 80 and 82. The Shield 60 has an array of Exit Orifices 90 circumferentially spaced at equal intervals about the Wall 66 in the proximity of the Ends 80 and 82 and a fluid Particulate Trap 100 disposed at the opposite end.

Referring now to FIG. 4, FIG. 2 and FIG. 5, there is shown a top and side view of the Partially Closed End 68 of the Shield 60 and frontal view of the Particulate Trap 100.

The Particulate Trap 100 has a fluid Receiving Cavity 102 adjacent to and communicating with the Partially Closed End 68 of Shield. The Receiving Cavity 102 is enclosed by a solid bottom Element 104, a Wall Element 106 and the Partially Closed End 68 of the Shield 60. The Partially Closed End 68 contains a fluid communications passage, such as an array of Openings 92 which link the Receiving Cavity 102 and Chamber 70 as shown in FIG. 4. The Wall Element 106 may be an extension of the Shield Wall 66 as shown or may be a separate element.

The Particulate Trap 100 has a fluid Entrance Port 110 passing through the Wall Element 106 for receiving a fluid flow into the Receiving Cavity 102. A Particulate Exit Port 112 having a smaller open area than the Entrance Port 110 is disposed through the Wall Element 106, opposite the Entrance Port 110, adjacent to Bottom Element 104.

In operation, the Oxygen Sensor 20 is immersed in a stream of heated exhaust gas (a fluid) with the Entrance Port 110 of the Particulate Trap 100 oriented into a component of the gas flow. Gas enters the Trap 100 through the Entrance Port 110 and is deflected and diverted through the Openings 92 of the End 68 into the Cavity 70. Carbon and most other particulates being heavier than the gas will tend to accumulate in the Receiving Cavity 102 and be blown out through the Exit Port 112 downstream of the Receiving Cavity 102. Prior to contacting the sensitive Element 30 the heated gas contacts the surfaces of the Shield 60 which act as a heat sink. Thus rapid rates of change in the temperature of the gas will be moderated before it flows over the ceramic zirconium dioxide Element 30.

The gas flows over the surface of the Element 30 in a direction parallel to the axis of the Element 30. The parallel flow over the Element 30 permits a larger percentage of the Exterior Coating 38 to be utilized. After the gas flows over the Element 30 it leaves the Shield 60 through the exit Orifices 90 at the housing end of the shield and then rejoins the mainstream of exhaust gases flowing within the exhaust system.

The velocity of the gas in Chamber 70 is reduced due to a decreased pressure gradient. This results from the increase in the length of the flow path for the diverted portion of the gas as compared to the shorter path taken by gas in the mainstream for a given pressure drop.

Protuberances on the inner surfaces of Walls 66 of the Shield such as shown on FIGS. 6 through 9 act as turbulence generators to aid the reaction of gases near the Layer 38 of catalytic material. Turbulent gas flow increases the volume of unreacted gas contacting the Layer 38 and helps remove gas adjacent to the Layer 38 that has already reacted with the oxygen ions. Gas turbulence therefore tends to increase the dynamic response and sensitivity of Oxygen Sensor 20.

Referring now to FIGS. 6 and 7, there is shown an alternate embodiment of the Shield 60 having such turbulence generators.

The Shield 120 shown in FIG. 6 is identical to the Shield 60 of FIG. 2 with the addition of elements protruding from the Wall 66 into the Chamber 70 towards Element 30. As shown in FIG. 7 those protruding elements may be a plurality of U-shaped Tabs 124 formed on the Wall 66 bent inwardly. The Opening 126 created by the bending of the Tabs 124 provides additional paths through which the exhaust gases can flow from the external environment to the sensitive Element 30.

It should be realized that the size of the various Entrance Port 110, Exit Port 112, the clearance between the Shield 60 and Element 30, and the number, size, shape and orientation of the turbulence generators will depend on such parameters as the sensor's thermal requirements and gas flow-through time.

An alternate configuration of the Shield 60 is shown in FIGS. 8 and 9.

A Shield 140 shown in cross section in FIG. 8 surrounds the tubular Element 30 and is similar to Shield 60 with the major distinction that the Partially Closed End 68 has been removed. The Shield 140 has a Wall 66 containing exit Openings 90, an Entrance Port 110, an Exit Port 112 and a Bottom Element 104.

A cylindrical Basket 144 as shown in FIG. 9 having an array of Tabs 150 protruding inwardly from the Walls 146, is pressed into Shield 140 as shown in FIG. 8. The Basket 144 further includes an End Plate 152 having an array of Openings 158 formed by Tabs 156 which protrude into the Basket 144. A particulate trap having a Receiving Cavity 102 is formed by End Plate 152, the Wall 66 and the Bottom Element 104 of Shield 140.

The operation of the previously described Shields 60, 120 and 140 requires that the Entrance Port 110 of the Particulate Trap 100 have a preferred orientation relative to the direction of the gas flow. In many applications, this may not be easy to achieve with a threaded connection of the sensor to an exhaust system. The particulate trap shown on FIG. 10 through 12 overcomes this directional requirement.

Referring first to FIGS. 10 and 11 there is shown a partial side view of an omni-directional Diverter 200. FIG. 11 is a sectional view illustrating the plurality of Receiving Cavities 202 of the Omni-directional Diverter 200.

The omni-directional Diverter 200 consists of a Bottom Plate 104 having a plurality of Walls 204 attached thereon radially extending from the center of the Bottom Plate 104. The Walls 204 forms a plurality of pie-shaped sectors 206. The upper portion of the Walls 204 are connected to the End 68 and the bottom plate 204, therein forming a plurality of symmetric radially extending pie-shaped Receiving Cavities 202. In addition, each Cavity 202 contains a Fluid Entrance Port 208 and terminates in common particulate Exit Port 218. The End 68 contains at least one fluid communication passage, such as Opening 92 for each Receiving Cavity 202.

In an alternate embodiment as shown on FIG. 12, the Bottom Plate 212 may have a conical shape-producing funnel shaped Receiving Cavities 214. It is obvious that funnel shaped cavities could have been formed by contouring the End 68 and utilizing a flat bottom element.

The operation of the omni-directional Diverter 200 is similar to the operation of the Particulate Trap 100 with the exception that a preferred mounting orientation of the Entrance Port 110 relative to the mainstream of flow is not required due to the plurality of Entrance Ports 208. The circumferential arrangement of the Entrance Ports 208 permit fluid to be diverted from the mainstream regardless of the final orientation of the Sensor 20 to the Wall 26. Obviously, Sensor 20 and mainstream of flow must be so oriented that a component of flow is directed into a Receiving Cavity 208.

The primary function of the Diverter 200, when immersed into the mainstream of fluid flow, is to intercept a portion of fluid therefrom and divert it through the Openings 92 in End 68 and into the Chamber 70. Secondly the receiving cavities such as Cavities 202 or 214 also function as particulate traps to reduce the number of particulates entering the Chamber 70. Particulates accumulating in the upstream Receiving Cavities 202 or 214 will tend to be blown through the common Exit Port 218 and return to the mainstream of flow.

Two alternative embodiments of an omni-directional diverter having a single circumferential receiving cavity are shown in FIGS. 13 through 17. The Diverter 230 shown in FIGS. 13 and 14 contains a Circular Disk 232 cantilevered from the center of the Partially Closed End 68 by a Rod 234.

The Diverter 240 shown on FIGS. 15 and 16 comprises a Frustro-conical Member 242 which is attached to the center of the End 68, and forms a receiving cavity having an ever-decreasing cross-section as measured along a decreasing radius.

What is claimed is:

1. A protective shield for protecting the sensing element of a sensor of the type which generates signals in response to a particular constituent of a fluid stream, wherein the sensor includes a housing and where the sensing element protrudes therefrom, the protective shield comprising:

shield means, for protecting said sensing element from direct contact with particulates within the fluid stream, said shield means surrounding the protruding portion of the sensing element and spaced therefrom to form a chamber about said sensing element, said shield means having one end adapted to fit to said housing and an opposite end, said shield further having fluid exit ports proximate to said one end, permitting fluid to flow out of said chamber, said shield means further having turbulence generating means for causing fluid flow to become turbulent disposed along its interior, including tabs protruding therefrom;

particulate trap means protruding into said fluid stream attached to said opposite end of said shield means for directionally intercepting a portion of the fluid stream, including a member having a top element attached to said opposite end of said shield means, a bottom element spaced a predetermined distance from said top element and a wall connecting said top element and said bottom element to form an enclosed fluid receiving cavity, said wall having a fluid entrance port directed into said fluid stream interconnecting the external fluid stream with said fluid receiving cavity; and where said top element further has a fluid communications passage connecting said fluid receiving cavity with said chamber.

2. The protective shield as recited in claim 1 wherein said particulate trap means contains a particulate exit port in said wall for permiting particulates to exit therefrom.

3. A protective shield for protecting the sensing element of a sensor of the type which generates a signal in response to a particular constituent of a fluid stream, wherein the sensor includes a housing and where the sensing element protrudes from said housing, the shield comprising:

shield means for protecting said sensing element from particulates within the fluid stream, formed as a cup-like element surrounding and spaced from said sensing element forming a chamber therebetween, said shield means having an open end attached to said housing and an opposite end having at least one entrance aperture proximate said opposite end passing therethrough and fluid exit ports passing through said shield proximate said open end, said shield means further having turbulence generating means for causing fluid flow to become turbulent disposed along its interior, including tabs protruding therefrom;

particulate trap means protruding into said fluid stream disposed between said shield means and the fluid stream for directionally intercepting a portion of the fluid, and for removing particulates from said intercepted portion of the stream and after removal of the particulates for diverting a portion of the fluid stream into said chamber through said at least one entrance aperture passing through said opposite end including:

a second cup-shaped member attached to said opposite end of said shield means having an open end, a bottom and a wall joining said open end to said bottom forming a fluid receiving cavity, said second cup-shaped member having a fluid entrance port, directed into said fluid stream, within said wall intercepting a portion of the fluid stream causing it to flow into said fluid receiving cavity wherein the fluid stream is caused to flow out of said fluid receiving cavity through said at least one entrance aperture wherein the deflection of said stream causes the removal of particulate matter from said intercepted portion of the fluid stream.

4. The protective shield as recited in claim 3 wherein said particulate trap means contains a particulate exit port in said wall for permiting particulates to exit therefrom.

5. A fluid sensor for detecting a constituent of a fluid stream comprising:

sensor means for generating a signal in response to a particular constituent of the fluid stream, said sensor means having a housing and a tubular shaped sensing element protruding from said housing;

shield means, for protecting said sensing element from direct contact with particulates within the fluid stream, said shield means surrounding the protruding portion of the sensing element and spaced therefrom to form a chamber about said sensing element, said shield means having said one end attached to said housing and having fluid exit means proximate said one end, for permitting fluid to flow out of said chamber and return to said fluid stream including:

said shield means further having turbulence generating means for causing flow to become turbulent disposed along its interior including tabs protruding therefrom;

particulate trap means protruding into said fluid stream attached to said opposite end of said shield means for directionally intercepting a portion of the fluid stream, for removing particulates from the intercepted portion of the fluid stream prior to the fluid entering said chamber and for diverting the intercepted portion of said fluid stream, with particulates removed, into said chamber including:

a member having a top element attached to said opposite end of said shield means, a bottom element spaced a predetermined distance from said top element and a wall connecting said top element and said bottom element forming an enclosed fluid receiving cavity, said wall having a fluid entrance port directed into said fluid stream interconnecting the external fluid stream with said fluid receiving cavity; and where said top element further has a fluid communications passage connecting said fluid receiving cavity with said chamber.

6. The sensor as recited in claim 5 wherein said particulate trap means contains a particulate exit port in said wall for permitting particulates to exit therefrom.

7. A fluid sensor for detecting a constituent of a fluid stream comprising:

sensor means for generating a signal in response to the particular constituent of the fluid stream, said sensor means having a housing and a tubular shaped sensing element protruding therefrom;

shield means formed as a cup-like element surrounding and spaced from said sensing element forming a chamber therebetween, said shield means having an open end attached to said housing and an opposite end having at least one entrance aperture passing therethrough, and fluid exit ports passing through said shield means proximate said open end, said shield means further having turbulence generating means for causing fluid flow to become turbulent disposed along its interior, including tabs protruding therefrom;

particulate trap means protruding into said fluid streams disposed between said shield and the fluid stream for directionally intercepting said fluid stream and for removing particulates from the intercepted portion of said fluid stream and for diverting a portion of the fluid stream, after the removal of the particulates, into said chamber through at said at least one entrance aperture prior to being communicated to said chamber and including:

a second cup-shaped member attached to said opposite end of said shield means having an open end, a bottom and a wall joining said open end to said bottom forming a fluid receiving cavity, said second cup-shaped member having a fluid entrance port directed into said fluid stream within said wall, intercepting a portion of the fluid stream and causing it to flow into said fluid receiving cavity wherein the fluid stream is deflected to flow out of said receiving cavity through said at least one entrance aperture wherein the deflection of said stream causes the removal of particulate matter from said intercepted portion of the fluid stream.

8. The sensor as recited in claim 7 wherein said particulate trap means contains a particulate exit port in said wall for permitting particulates to exit therefrom.

9. A particulate trap in combination with a shield of a fluid sensor for sensing a constituent in a fluid stream wherein said shield surrounds the fluid sensor forming a chamber therebetween, said particulate trap comprising:

a cylindrical housing located within the fluid stream having a top attached to said shield, a bottom, and a wall, forming a fluid receiving cavity, said wall having a fluid entrance port interconnecting the fluid to be sensed with said fluid receiving cavity and said top having a fluid communicating passage including at least one hole connecting said fluid receiving cavity with said chamber wherein said at least one hole is located 90° relative to said fluid entrance port and where said fluid receiving cavity contains a particulate exit port within said wall opposite said fluid entrance port having an area less than the area of said fluid entrance port.

10. A sensor for sensing the oxygen concentration in a stream of heated exhaust gases in the exhaust system of an engine and for generating an electrical signal in response thereto, said sensor comprising:

a housing adapted to be attached to an opening in the exhaust system;

a tubular shaped sensing element protruding from said housing including a zirconium dioxide element;

a shield attached to said housing for protecting said sensing element from particulates within the exhaust gases; said shield surrounding the protruding portion of the sensing element and spaced therefrom to form an annular chamber about said sensing element, said shield having one end attached to said housing and an opposite end, said shield further having fluid exit means proximate said one end, for directing fluid out of said annular chamber, said shield further including turbulence generating means for causing fluid flow to become turbulent disposed along its interior, including tabs protruding therefrom;

particulate trap means protruding into said fluid stream attached to said opposite end of said shield for directionally intercepting a portion of said fluid stream, for removing particulates from the intercepted portion of the fluid stream, and for diverting the intercepted portion of said fluid stream, with particulates removed, into said annular chamber formed between the shield and the sensing element including:

a second housing enclosing a fluid receiving cavity, said second housing having a top attached to said opposite end of said shield, a bottom, and a wall, said wall having a fluid entrance port directed into said fluid stream interconnecting the external fluid stream with said fluid receiving cavity and said top having a fluid communication passage interconnecting said fluid receiving cavity with said annular chamber.

11. The sensor as recited in claim 10 wherein said particulate trap means contains a particulate exit port in said wall for permitting particulates to exit therefrom.

12. A sensor for sensing the oxygen concentration in a stream of heated exhaust gases in the exhaust system of an engine and for generating an electrical signal in response thereto, said sensor comprising:

a housing adapted to be attached to an opening in the exhaust system;

a tubular shaped sensing element protruding from said housing including a zirconium dioxide element;

a shield attached to said housing for protecting said sensing element from particulates within the exhaust gases, said shield formed as a cup-like element surrounding and spaced from said sensing element forming an annular chamber therebetween, said shield having an open end attached to said housing, an opposite end having at least one hole therethrough, a cylindrical wall linking said open end and said opposite end, and where said cylindrical wall contains fluid exit means, proximate said open end, for directing fluid out of said annular chamber;

said shield further including turbulence generating means for causing fluid flow to become turbulent disposed along its interior, including tabs protruding therefrom;

particulate trap means protruding into said fluid stream disposed between said shield and the fluid stream for communicating a portion of the stream to said annular chamber through said opposite end for removing particulates from the intercepted portion of the stream prior to being communicated to said chamber and contact with said sensing element, including:

a hollow cylindrical member having a wall attached to said opposite end of said shield and having a fluid entrance port directed into said fluid stream and a fluid receiving cavity within said wall wherein said fluid entrance port intercepts a portion of the fluid stream causing it to flow into said fluid receiving cavity wherein particulate matter is removed from said intercepted portion of the fluid stream and the stream is then directed to flow through said at least one hole into said annular chamber and out through said fluid exit means of said shield.

13. The sensor as recited in claims 12 wherein said particulate trap means contains a particulate exit port in said wall for permitting particulates to exit therefrom.

* * * * *